United States Patent [19]
Jones et al.

[11] Patent Number: 5,866,112
[45] Date of Patent: Feb. 2, 1999

[54] METHODS OF ODOR TREATMENT

[75] Inventors: Craig Jones, Juno Beach; D. Michael Bitz, Miami, both of Fla.

[73] Assignee: E.K.M.A., Inc., Miami, Fla.

[21] Appl. No.: 476,374

[22] Filed: Jun. 7, 1995

Related U.S. Application Data

[63] Continuation-in-part of Ser. No. 376,553, Jan. 20, 1995.
[51] Int. Cl.$^6$ .............................. A61L 11/00; A61L 9/01; A61K 38/46
[52] U.S. Cl. .................. 424/76.6; 424/76.8; 424/76.9; 424/94.1; 424/94.6
[58] Field of Search ................. 424/76.6, 76.8, 424/76.9, 94.1, 94.6

[56] References Cited

U.S. PATENT DOCUMENTS

| | | | |
|---|---|---|---|
| 2,196,361 | 4/1940 | Liebesny | 195/79 |
| 2,767,072 | 10/1956 | Coanda | 71/7 |
| 3,095,359 | 6/1963 | Heller | 195/78 |
| 3,623,265 | 11/1971 | Brunton et al. | 47/1.3 |
| 3,675,367 | 7/1972 | Amburn | 47/1.3 |
| 3,871,961 | 3/1975 | Gianessi | 195/37 |
| 4,487,766 | 12/1984 | Mach | 424/180 |
| 4,508,625 | 4/1985 | Graham | 210/695 |
| 4,828,710 | 5/1989 | Itoh et al. | 210/675 |
| 4,879,045 | 11/1989 | Eggerichs | 210/695 |
| 4,915,915 | 4/1990 | Treharne | 422/186.24 |
| 4,938,875 | 7/1990 | Niessen | 210/695 |
| 5,549,729 | 8/1996 | Yamashita | 71/26 |

FOREIGN PATENT DOCUMENTS

| | | |
|---|---|---|
| 224 615 | 7/1985 | Germany . |
| 6174629 | 4/1986 | Japan . |
| 62-278907 | 3/1987 | Japan . |
| 0235987 | 2/1990 | Japan . |
| 324680 | 12/1971 | U.S.S.R. . |
| WO 93/13725 | 7/1993 | WIPO . |
| WO 96/22359 | 7/1996 | WIPO . |

OTHER PUBLICATIONS

Curtis, Tom "The Old Man and the Secret", Texas Monthly 18(6):112 (1990).
JP Patent 362129694 A abstract, see entire 1994 abstr.
EPO, US 004898738A, Feb. 6, 1990, Yamamoto et al abstr.

*Primary Examiner*—David M. Naff
*Assistant Examiner*—Deborah K. Ware
*Attorney, Agent, or Firm*—Nixon & Vanderhye P.C.

[57] ABSTRACT

The present invention relates to a composition capable of reducing or eliminating offensive odors emanating from sites including, animal holding areas, animal waste areas, feed lots, water holding areas, landfills, trash transfer centers and leachate reservoirs. The composition comprises an acid component, or salt thereof, an iron component and a nitrogen source. The invention also relates to a method of odor reduction or elimination based on the above-described composition. Furthermore, the composition utilized in the disclosed methods includes a polysaccharide hydrolase component, and at least one molybdenum, copper and/or gum component.

12 Claims, 2 Drawing Sheets

METHODS OF ODOR TREATMENT

This is a continuation-in-part of application Ser. No. 08/376,553, filed Jan. 20, 1995, the entire contents of that application being incorporated herein by reference.

TECHNICAL FIELD

The present invention relates to a composition capable of reducing or eliminating odors and to a method of odor reduction or elimination based on same.

BACKGROUND

Odor reducing or eliminating compositions have application in a number of areas. Of particular importance are those situations where the odors are sufficiently offensive to be problematic for individuals having to work in proximity with the odor producing material. Examples of such situations include cattle feed lots, swine barns, poultry houses and the like. In these settings, the ability to reduce or eliminate odor production would greatly enhance the quality of the working environment. The present invention provides a composition suitable for use in such settings.

OBJECTS AND SUMMARY OF THE INVENTION

It is a general object of the present invention to provide a composition capable of reducing or eliminating odors.

It is another object of the invention to provide a method of treating an odor producing source so as to reduce or eliminate odor production therefrom.

Having in mind the foregoing objects, the present invention relates, in one embodiment, to an odor-reducing composition comprising an acid component, an iron component and a nitrogen component.

In another embodiment, the present invention relates to a method of reducing or eliminating an offensive odor comprising contacting the compound responsible for the odor with the above composition under conditions such that the odor is eliminated or reduced.

In a further embodiment, the present invention relates to a method of inhibiting odor production at a source comprising contacting the source with the above composition under conditions such that the inhibition is effected.

Further objects and advantages of the present invention will be clear from the description that follows.

DETAILED DESCRIPTION OF THE INVENTION

The present invention relates to a method of reducing or eliminating odors and inhibiting the production thereof, and to compositions suitable for use in effecting that reduction/elimination or inhibition. The compositions of the invention can be used to reduce or eliminate odor production in a variety of settings including barns, poultry houses, kennels and other animal holding areas, feed lots, and areas where water is contained, such as lagoons. The composition can also be used in waste control area such as landfills, trash transfer centers, leachate reservoirs and animal disposal areas.

The composition of the present invention comprises an acid component or salt thereof such as citric acid, acetic acid, ascorbic acid, malic acid or tartaric acid, an iron component, such as a ferric salt, for example, ferric chloride, and a nitrogen source, such as urea. The composition can further comprise one or more of the following: a molybdenum component, for example, molybdic acid or salt thereof a copper component, for example, copper sulfate, aloe vera and a gum component, such as xanthan gum or guar gum. In addition, the composition of the invention can include an enzyme component derived from a microbial culture supernatant or prepared from polysaccharide hydrolases such as starch hydrolases, including α-amylase and glucoamylase, and galactomannan hydrolases, such as hemicellulase.

When the enzyme component of the composition is derived from a microbial culture supernatant, the following preparative procedure can be used.

Starting cultures can be obtained by combining isolates of specific microbial strains or by obtaining a mixed culture from an animal, for example, from the gastrointestinal track of an animal, preferably, a mammal, more preferably a herbivore, most preferably a cow (eg a lactating cow). Starting cultures can be obtained, for example, from a sample aspirated from the stomach of an animal (eg from the rumen of a herbivore) or from a fecal sample taken from the intestinal track of an animal.

Figure 1:
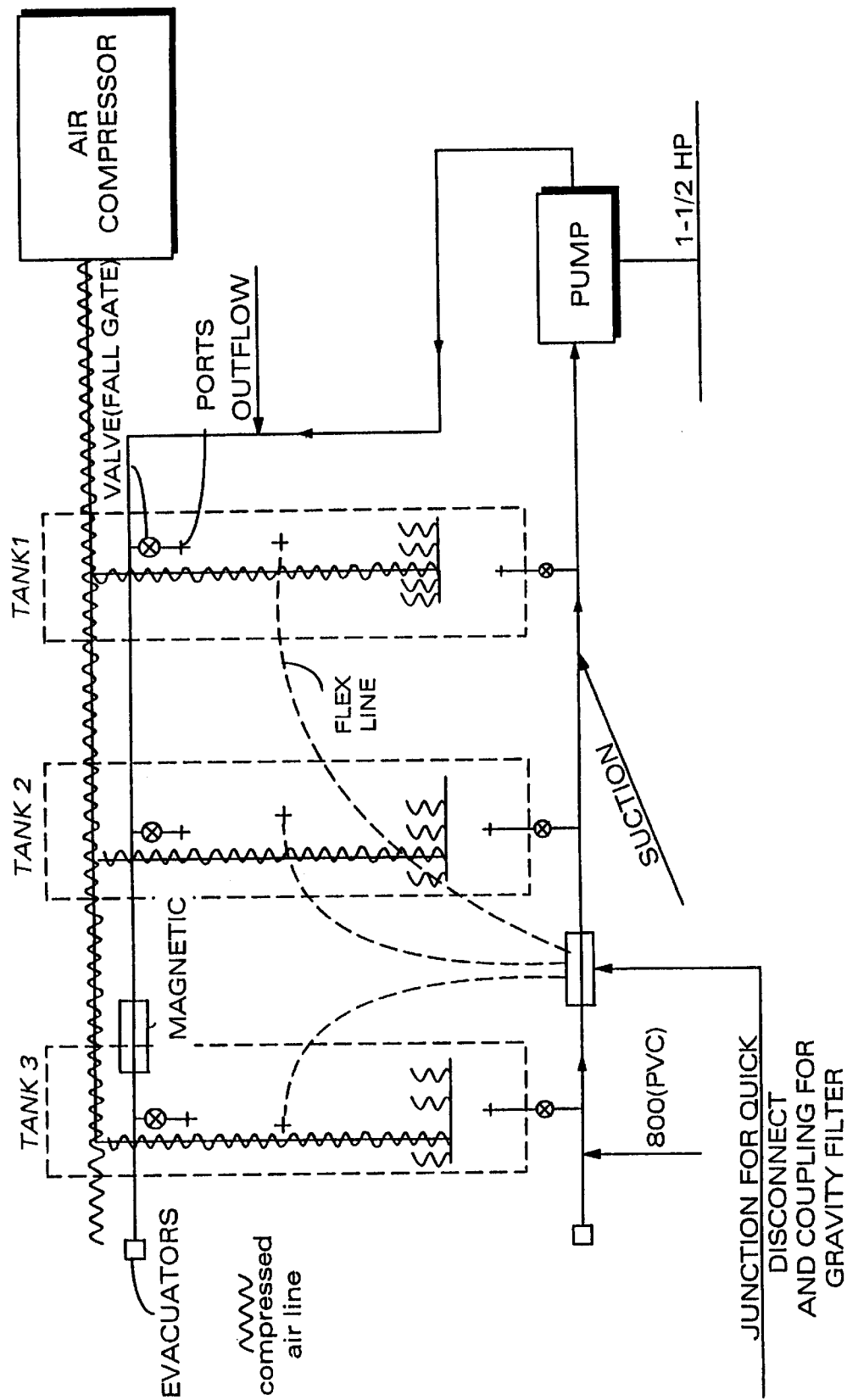
FIG. 1. Diagram of fermentation tanks for preparation of microbial cultures. The line through the junction is 1½" diameter, the flex line is 1½" and the ports are 1½".

The starting culture, whether obtained from a natural source or prepared from isolates, is cultured for an initial period (eg 21 to 31 hours, preferably, 24 hours) in the presence of a medium that can be prepared from natural sources (eg from the saliva of a herbivore (eg a cow)) or from chemicals (culturing can be carried out in a container such as Tank 1 of FIG. 1). When prepared from saliva, the following procedure can be used. A bolus (eg about 1 liter) is taken from the mouth of the animal (eg a cow) and placed on a filter (eg about an 80 micron filter). The bolus is washed with warm water (about 10 liters of water per liter of bolus) and the filtrate (pH preferably about 6.3 to 6.8) is obtained and used as the initial culture medium.

When synthetic medium is used, it is preferably formulated so as to contain the following:
sodium
potassium
calcium
magnesium
inorganic phosphorus
chloride As an example, a culture medium containing the following can be used:

| | |
|---|---|
| Sodium bicarbonate | .0225 g/liter |
| Potassium bicarbonate | .00125 g/liter |
| Calcium carbonate | .000025 g/liter |
| Magnesium carbonate (anhydrous) | .0000375 g/liter |
| Phosphoric acid | .003375 g/liter |
| Chloroacetic acid | 002125 g/liter |

The concentrations of the culture medium components can vary depending, for example, on the starting culture, however, typically concentrations vary, for example, by plus or minus 45%, preferably, plus or minus 20% from the above.

The starting culture sample is incubated in the culture medium, preferably, at a pH in the range of 6.9 to 7.3. Adjustments in pH can be made at this point and throughout the process using a variety of acids and bases, sulfuric, hydrochloric and citric being the preferred acids, citric being more preferred, and potassium hydroxide, calcium hydroxide and sodium bicarbonate being the preferred bases, sodium bicarbonate being most preferred. During this initial incubation period, and throughout the process, air is introduced (eg by compressed air injection) to maintain an oxygen content in the range of 3 to 5 ppm. During this initial period, nitrogen, sugar and oxygen uptake occurs. Cells increase in number, nutrient content and in cell-wall content.

A food source (substrate) is subsequently (eg after about 23 to 28 hrs, preferably 24 hrs) added to the medium/starting culture sample mixture. The food source can comprise a mixture of feed grains and grasses. Preferably, at least three of the following are added in approximately equal parts by weight:

crushed corn
oats
milo
alfalfa
sunflower seeds
peanuts (whole)
wheat
soybeans
barley
rice
flax.

Alfalfa, wheat, soybeans and barley are preferred. The food source is typically added to the medium/starting culture sample together with a further volume of liquid (ie culture medium and water (eg in a ratio of about 1:5 to 1:4)) in a ratio of about 1 kg of dry matter to about 7–8 liters of liquid. Multiple additions of food source and liquid to the original medium/starting culture sample can be made, 2 additions at approximately 24 hour intervals being preferred.

Throughout this period of incubation, an approximately neutral pH is maintained, a pH in the range of about 6.9 to about 7.3 being preferred. The temperature is maintained, preferably, in the range of about 34° to 41° C., 37° to 40° C. being preferred.

After the final addition of food substrate, the resulting broth is well mixed, for example, by recirculating the broth in a recirculation tank. The recirculation is typically for a period of about 24 hours, after which time the broth is allowed to stand for a period sufficient to allow the particulate matter to settle out.

An aliquot of the broth supernatant is then removed and placed in a second container (eg a tank such as Tank 2 of FIG. 1). By separating the supernatant aliquot from the particulate matter, the microorganisms present in the aliquot are separated from their food source (thereby causing a "secondary shunt metabolism" to be effected). The pH of the transferred aliquot is slowly reduced (eg over a period of several hours) to about 4.5 to about 6.3, 5.8 to 6.3 being preferred. The temperature is maintained in the range of about 34° C. to 41°, 37° to 41° C. being preferred. A minimal amount of a second food source is added (eg about 1%–3% v/v of the aliquot, 3% being preferred). The second food source is, for example, molasses (eg sugar cane or citrus molasses), aloe vera, papaya juice, stearate or glycogen. Glycogen, aloe and citrus molasses are preferred.

At this point in the process, the number of cells per ml is, advantageously, in the range of 700,000 to 1.5 million, about 850,000 cells/ml to 900,000 cells/ml being preferred, around 890,000 cells/ml being most preferred. The cell count can be increased by delaying the transfer of the aliquot from the first tank to the second.

Figure 2A:
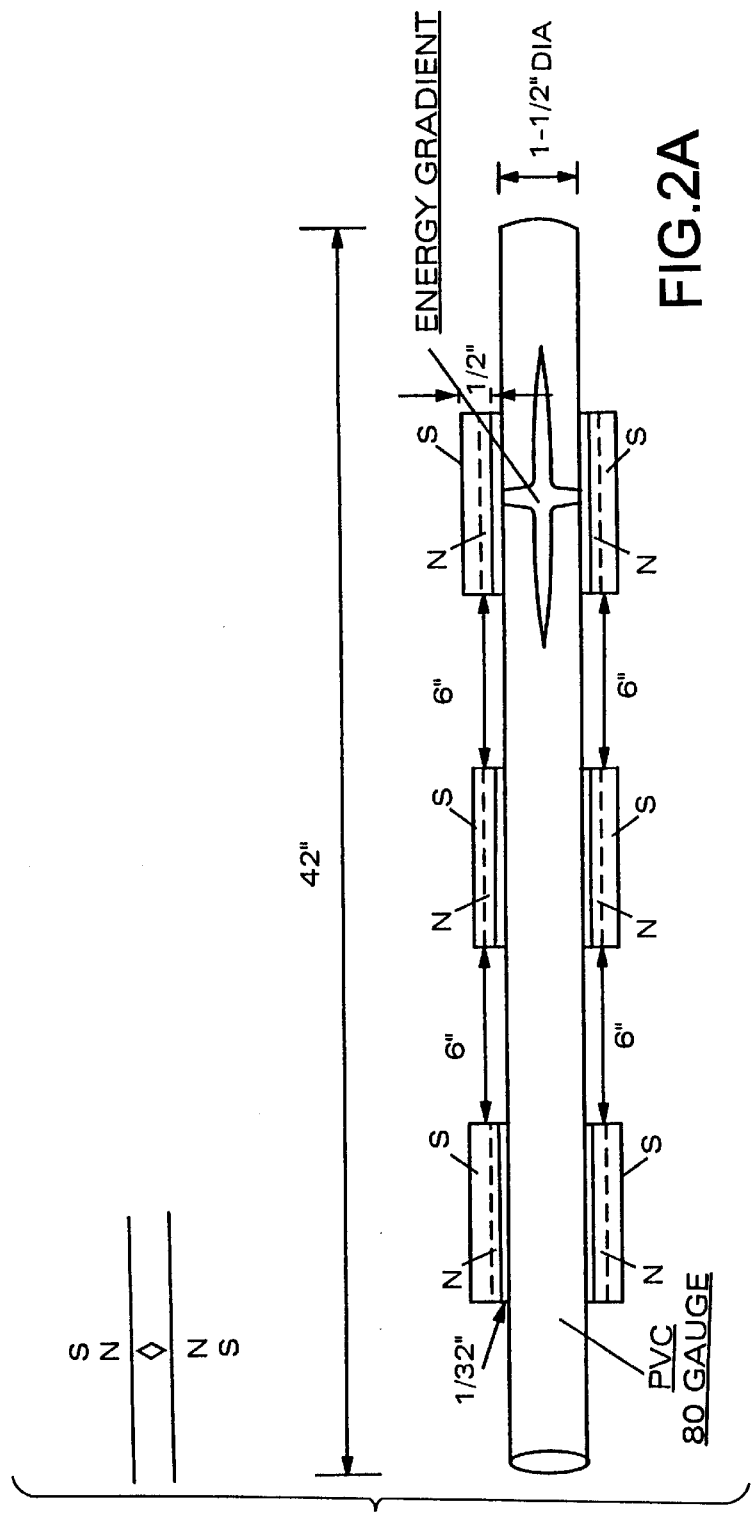
FIG. 2. Diagram of orientation of magnets relative to recirculation tube.
Figure 2B:
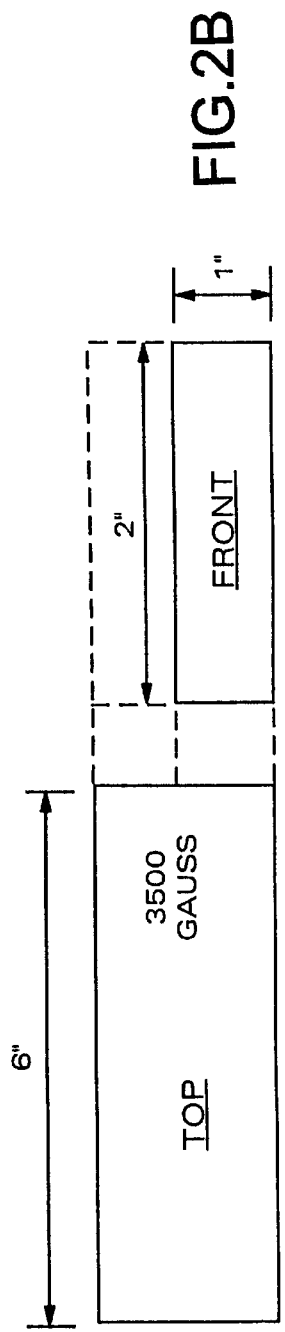

After the pH has been reduced and the second food source added, an aliquot of the culture (eg transferred to a tank such as Tank 3 of FIG. 1) is recirculated through a magnetic field. The field is created using an electromagnet or permanent magnets, for example, rare earth magnets. In the case of permanent magnets, an appropriate field can be created, for example, by two opposing magnets. Magnets suitable for use in the present invention have a strength in the range of 1200 to 4500 gauss, about 3500 gauss magnets being preferred. FIG. 2 includes a diagram of a preferred orientation of such magnets. While, in the Figure, like poles (ie north poles) are shown to face either side of the recirculation tube, such need not be the case (e.g. opposite poles can also face the tube).

The exposure of the microorganisms to the magnetic field results in an increase in the thickness of the microbial cell wall and an increase in cell mobility, as viewed under light microscopy. The invention contemplates the use of magnetic fields that can achieve these ends.

During the process of recirculation through the magnetic field, a formulation of nutrients is added that can include Na, Cl, P, Mg, Ca, S, Zn, Cu, Fe, K, Mn, Mo, Si, B, Ni, and Rb, preferably, also Co, I, or Se. Preferably, the formulation has the following composition and the concentration ranges listed (g/l) reflect the increase in concentration of the components in the culture upon addition of the formulation to the culture:

|  | Broad range (g/l) | Preferred Range (g/l) |
| --- | --- | --- |
| Sodium bicarbonate | .0001–.10 | .0005–.090 |
| Chloroacetic acid | .0001–.04 | .0005–.03 |
| Phosphoric acid (liquid) | .001–.05 | .002–.02 |
| Magnesium carbonate (anhydrous) | .000075–.05 | .001–.004 |
| Calcium carbonate | .000250–.300 | .001–.004 |
| Sulfur (from sulfates in compositon) | .000075–.04 | .002–.006 |
| Zinc stearate | .00004–.008 | .0003–.005 |
| Copper sulfate | .00000001–.06 | .00000001–.00001 |
| Cobalt acetate tetrahydrate | .0000005–.0000000006 | .00000004–.000000003 |
| Iodine (liquid) | .000000003–.000006 | .00000005–.000000008 |
| Se (plasma grade std (liquid)) | .000000003–.00001 | .00000002–.000001 |
| Iron sulfate | .0000002–.00009 | .000005–00006 |
| Potassium bicarbonate | .05–.0006 | .04–.006 |
| Manganese sulfate monohydrate | .000005–.0045 | .00045–.00003 |
| Molybdic acid 85% (powder) | .00000001–.00004 | .00000019–.000005 |
| Silicon (reference std solution (1000 ppm)) | .0000005–.0005 | .00005–.0001 |
| Boric acid | .000002–.0000000003 | .00000003–.0000002 |
| Nickle carbonate | .000000005–.00005 | .0000005–.000003 |
| Rubidium chloride | .000000009–.0000095 | .00000006–.00000055 |

Other forms of the indicated elements can also be used so long as they are acceptable to the microorganisms.

Upon completion of the magnetic field exposure and nutrient formulation addition, the resulting composition can be processed (eg filtered or centrifuged) so as to remove the microorganisms and then used immediately or stored, for example, for as long as two years and the microorganisms removed prior to use. During storage, the pH is maintained, preferably, between 5.5 and 6.5 and the temperature between 5° C. and 45° C., a temperature in the range of 34°–41° C. being preferred. Storage in the absence of ultra violet light is preferred.

To remove microorganisms from the composition resulting from the process described above, aliquots of the composition can be centrifuged, for example, first at a low speed (eg about 3500 rpm) and for a short duration (eg about 5–10 min). The resulting supernatant can then be recentrifuged (preferably under refrigeration) at a greater speed (eg about 20,000 rpm or up to about 45,000 g) for a longer time (eg about an hour or longer) to pellet cell walls and other cellular debris that may be present. One skilled in the art will appreciate that any of a number of centrifuges can be used, including, for example, a Beckman J-25 centrifuge. One skilled in the art will also appreciate that a variety of filtration processes can be used to remove the microorganisms.

Upon removal of the cells and cellular debris, the resulting supernatant (filtrate) is assayed to ensure that appropriate concentrations of enzymes (eg amylase, and hemicellulase and/or glucanase) are present. Typically, amylase activity is assayed using a calorimetric visual endpoint determination. Kits are commercially available for conducting such assays, one such kit being available from Sigma Chemical Company (eg catalog numbers 577–250 and 577-M). The time required for sucrose-starch mixtures, when treated with iodine solution, to change from blue to reddish-brown is inversely proportional to amylase activity. The amylase activity of the supernatant (filtrate) is preferably at least 45,000–45,4000 ct/ml. Amylase levels can be adjusted by combining aliquots of the composition resulting from the culture process described above, processed to remove intact microorganisms and cellular debris.

Hemicellulase levels in the resulting supernatant (filtrate) are advantageously at least 2,000 ct/mg. Hemicellulase levels can be measured using a βgalactase dehydrogenase system (locust bean gum substrate). A commercial kit for such purpose can be used (eg Sigma H 0771).

Table 1 below includes preferred components of the composition of the invention and concentration ranges at which those components can be present in the composition.

TABLE I

|  | Preferred Range mg/ml |  | Range mg/ml |  |
| --- | --- | --- | --- | --- |
| Citric Acid | .001 | .020 | .0001 | .100 |
| Ferric Chloride | .0008 | .000011 | .008 | .0000011 |
| Molybdenum | .0008 | .000011 | .008 | .0000011 |
| Copper Sulfate | .0008 | .000011 | .008 | .0000011 |
| Urea | .100 | .003 | 1.000 | .0003 |
| Aloe Vera | 2.100 | .600 | 3.000 | .003 |
| Xanthan Gum | 2.100 | .600 | 3.000 | .003 |
| Guar Gum | 2.100 | .600 | 3.000 | .003 |
| Culture supernatant or filtrate | 3.00 | .600 | 5.000 | .003 |
| pH of Water base | 3.5 | 4.5 | 3.0 | 5.0 |

Table II includes a specific composition suitable for use in the present invention.

TABLE II

| 1. Citric Acid (Food grade) (HMIS Anhydrous) |  |  | .002% |
| --- | --- | --- | --- |
| 2. Ferric Chloride (Anhydrous) |  |  | .00011% |
| 3. Molybdenum (Molybdic Acid 85% Powder) |  |  | .00011% |
| 4. Copper (Copper Sulphate) |  |  | .00011% |
| 5. Urea (Feed Grade) 45% |  |  | .05% |
| 6. Aloe Vera | 10/50% | Viscosity[1] | 1.6% |
| 7. Xanthan Gum | 30/50% | Viscosity | 1.6% |
| 8. Guar Gum | 30/50% | Viscosity | 1.6% |
| 9. Culture supernatant | 20/50% | Viscosity | 1.0% |

[1]Viscosity can be measured using a viscometric tube, stop watch and temperature using carboxy methylcellulose as the standard.

| 1 Poise (P) = 0.1 Pa'S mPa's (=CP) CP = Centi Poise |  |  |  |
| --- | --- | --- | --- |
|  | % Concentration | (CP) | % Vol./Sol |
| Aloe Vera | 50% | 2500 CP | 1.6% |
| Xantham Gum | 1% | 600 CP | 1.6% |
| Guar Gum | 1.5% | 15000 CP | 1.6% |
| Culture | 50% | 4300 CP | 1.6% |

The composition of the invention can be specifically formulated to suit a specific application need. For example, when an odor-producing source is exposed to UV light, the composition can be formulated to include a UV protectant (eg sodium alginate, a microbial gum). Further, when the odor-producing source is exposed to drying conditions, the composition can be formulated (eg with a gum) so as to render it capable of retaining its moisture content.

The composition of the present invention can be used alone or in combination with disinfectants and/or perfumes, depending on the odor problem to be addressed. When such disinfectants, perfumes, etc are used, they can be applied separately or co-formulated with the composition of the invention using known formulating techniques.

Application of the composition of the present invention can be carried out in a variety of ways as convenient in view of the odor-producing source. For example, the composition can be provided as an aerosol into the atmosphere surrounding the odor-producing source, thereby effecting direct contact with the odor-producing molecules in the air and, upon settling to the ground, with the odor-producing source. The composition can likewise be directly applied to the odor-producing source by, for example, pouring, spraying, etc, the composition onto the source. It will be appreciated that the number of applications of the compositions will vary with the particular odor problem being addressed. In the case of water containment situations such as lagoons, where short carbons chains are involved, the application can be, for example, 1 oz/1000 gallons per week.

While not wishing to be bound by any particular theory it is believed that the odor-producing sources to which the present method and composition have applicability are contaminated with microbes (eg anaerobes and aerobes), the metabolism of which is believed to result in the release of aromatic compounds into the environment that are offensive to the olfactory system. It is also believed that the composition, on contact with the airborne odiferous aromatic compounds, chemically reacts therewith in a manner that results in decomposition of the aromatic compounds to products having an acceptable odor. The composition of the present invention, upon contact with the odor-producing source (eg microbially contaminated animals, feces, feed and the like), is believed to alter the microbial population thereof in favor of aerobic organisms (or metabolism in the case of facilitative anaerobes). Aerobic metabolism of the source by the microbes present therein is believed to result in the release of more acceptable (from an odor standpoint) products into the environment.

All documents cited above are hereby incorporated in their entirety by reference.

One skilled in the art will appreciate from a reading of this disclosure that various changes in form and detail can be made without departing from the true scope of the invention.

What is claimed is:

1. A method of reducing or eliminating an offensive odor emanating from a source selected from the group consisting of an animal holding area, an animal disposal area, a feed lot, a water holding area, a landfill, a trash transfer center, and a leachate reservoir, comprising contacting said source with a composition comprising an acid component, or salt thereof, an iron component, a nitrogen component, a polysaccharide hydrolase component and at least one of a molybdenum component, a copper component, and a gum component in an effective amount to reduce or eliminate said odor emanating from said source.

2. A method of inhibiting offensive odor production at a source selected from the group consisting of an animal holding area, an animal disposal area, a feed lot, a water holding area, a land fill, a trash transfer center, and a leachate reservoir, comprising contacting said source with a composition comprising an acid component, or salt thereof, an iron component, a nitrogen component, a polysaccharide hydrolase component and at least one of a molybdenum component, a copper component, and a gum component in an effective amount to inhibit said odor production at said source.

3. The method according to claim 1 or 2 wherein said hydrolase is a starch hydrolase.

4. The method according to claim 3 wherein said starch hydrolase is α-amylase or glucoamylase.

5. The method according to claim 1 or 2 wherein said hydrolase is a galactomannan hydrolase.

6. The method according to claim 5 wherein said galactomannan hydrolase is hemicellulase.

7. The method according to claim 1 or 2 wherein said acid is ascorbic, citric or acetic acid, or salt thereof.

8. The method according to claim 1 or 2 wherein said composition further comprises an ultra violet protectant.

9. The method according to one of claims 1 and 2 wherein said odor emanates from feces.

10. The method according to one of claims 1 and 2 wherein said odor emanates from an animal.

11. The method according to one of claims 1 and 2 wherein said odor emanates from animal feed.

12. The method according to one of claims 1 and 2 wherein said source is microbially contaminated.

* * * * *